United States Patent [19]
Lauks

[11] Patent Number: 4,613,422
[45] Date of Patent: Sep. 23, 1986

[54] AMBIENT SENSING DEVICES
[75] Inventor: Imants R. Lauks, Sewell, N.J.
[73] Assignee: Integrated Ionics Inc., Dayton, N.J.
[21] Appl. No.: 572,199
[22] Filed: Jan. 19, 1984
[51] Int. Cl.$^4$ .......................................... G01N 27/30
[52] U.S. Cl. .................................. 204/419; 204/416; 204/418
[58] Field of Search ............... 204/414, 415, 416, 418, 204/419, 420, 433; 128/635; 357/23 I, 25

[56] References Cited
U.S. PATENT DOCUMENTS

| | | | |
|---|---|---|---|
| 3,911,901 | 10/1975 | Niedrack et al. | 204/414 X |
| 3,923,627 | 12/1975 | Niedrack et al. | 204/414 |
| 3,926,766 | 12/1975 | Niedrack et al. | 204/414 X |
| 4,020,830 | 5/1977 | Johnson et al. | 204/426 X |
| 4,133,735 | 1/1979 | Afromowitz et al. | 204/420 X |
| 4,273,636 | 6/1981 | Shimada et al. | 204/415 |
| 4,456,522 | 6/1984 | Blackburn | 204/419 X |

OTHER PUBLICATIONS

G. Rechnitz, C & EN, pp. 29–35, Jan. 27, 1975.
Schiavone et al., "Improved Electrochromic Behavior of Reactively Sputtered Iridium Oxide Films", Journal of Elect. Soc., vol. 128, p. 1339 (1981).
Katsuke et al., "PH-Sensitive Sputtered Iridium Oxide Film", Sensors and Actuators, vol. 2, No. 4, p. 399 (1982).
Danielson et al., "Development of Electrical and Electrochem Probes for Down Hole and In-Line Chemical Analysis of High Pressure, High Temperature Geothermal Fluids", Nov. 1977.

Primary Examiner—John F. Niebling
Assistant Examiner—Nam X. Nguyen
Attorney, Agent, or Firm—Pennie & Edmonds

[57] ABSTRACT

A device for the measurement of ionic and gas species at high temperatures. Platinum metal oxides are used for the electrical signal paths between electrical elements on the device to make the device particularly adaptable to high temperature measurement applications. Chemically sensitive composite structures may be hardened for high temperature applications by mixing polyimide with the materials normally used in the outer layer of such structure.

22 Claims, 3 Drawing Figures

AMBIENT SENSING DEVICES

CROSS REFERENCE TO RELATED APPLICATIONS

Related applications are "Ambient Sensing Extended Gate Transistor, Ser. No. 572,182 Integrated Ambient Sensing Devices and Methods of Manufacture, Ser. No. 572,185 "Method of Calibrating Amorphous Metal Oxide Electrodes, Ser. No. 572,200 and Ambient Sensing Devices Using Polyimide, Ser. No. 512,213 filed concurrently herewith, and "Amorphous Metal Oxide Electrodes," Ser. No. 441,902, filed Nov. 15, 1982, which are incorporated herein by reference.

BACKGROUND OF THE INVENTION

This relates to ambient sensing electrodes and in particular to electrodes that are adapted for operation in high temperature environments and to structures for mounting such electrodes.

It frequently is necessary to monitor the composition of a chemical environment, for example, to regulate chemical or biochemical processes, to determine air or water quality, or to measure parameters of interest in biomedical, agricultural or animal husbandry disciplines. One means for the detection, measurement and monitoring of the chemical properties of a substance involves the measurement of potential difference between two electrodes with the potential difference being dependent upon the chemical activity being measured. Because of the nature of the chemical environment, it is desirable that any measurement apparatus have at least some of the properties of: low cost, simple fabrication methodology, digital operation, some degree of signal preconditioning or intelligence, small size, high chemical sensitivity with selectivity, multiple species information with specificity, choice of reversible or integrating response to chemical species, temperature insensitivity or compensation and low power operation. In addition the measurement apparatus should have good long term electrochemical stability, good physical resiliency and strength and good resistance to corrosion and chemical attack. In the case of electrical measurement devices, the devices should also have low electrical impedance to provide good signal to noise ratio and preferably a Nernstian response to the chemical phenomena being measured.

Bergveld has proposed that hydrogen and sodium ion activities in an aqueous solution be measured by a metal oxide semiconductor field-effect transistor (MOSFET) modified by removal of the gate metal. P. Bergveld, "Development, Operation, and Application of the Ion-Sensitive Field-Effect Transistor as a Tool for Electrophysiology" *IEEE Transactions of Biomedical Engineering*, Vol. BME-19, pages 342–351 (September, 1972). In particular, if a MOSFET with no gate metal were placed in an aqueous solution, Bergveld suggested that the silicon dioxide insulation layer would become hydrated and then, because of impurities in the hydrated layer, ion selective. After hydration of the insulation layer of the MOSFET, Bergveld believed the device could be used for ion activity measurement by immersing the device in the solution in question and then recording conductivity changes of the device. Thus, the Bergveld device is commonly referred to as an ion-sensitive field effect transistor (ISFET).

Bergveld's work led to other developments in the field of ion sensitive electrodes such as the chemical sensitive field effect transistor (CHEMFET) device described in U.S. Pat. No. 4,020,830 which is incorporated herein by reference. As described in the '830 patent, the CHEMFET is a MOSFET in which the gate metal has been replaced by a chemically selective system that is adapted to interact with certain substances to which the system is exposed. Thus as shown in FIGS. 1 and 2 of the '830 patent, the CHEMFET is identical in structure to a MOSFET except for a membrane 38 that is deposited in place of a metal gate layer on the oxide insulator above the channel region of the transistor and, optionally, an impervious layer 44 that covers all other parts of the CHEMFET that might be exposed to the solution. Numerous variations on CHEMFET structures are disclosed, for example, in U.S. Pat. Nos. 4,180,771, 4,218,298, 4,232,326, 4,238,757, 4,305,802, 4,332,658, 4,354,308, 4,485,274 and 4,397,714. Further improvements in these structures are disclosed in Application Ser. No. 441,902.

Despite this intense development of new designs, there is still considerable work to be done to achieve some of the desirable transducer properties described above. One area in which improved electrodes are needed is the field of high temperature sensing. High temperature environments are typically extremely hostile to electrodes, causing the electrodes to deteriorate so fast that they cannot practically be used in many environments. For example, it is extremely useful to be able to sense ambient conditions in a borehole such as an oil well. However, these environments are often extremely hot and possibly corrosive as well. While information about the chemistry of this environment would be extremely desirable, the cost of obtaining it with conventional electrodes, which cannot survive in this environment for any period of time, cannot be justified.

SUMMARY OF THE INVENTION

I have devised improved apparatus for the measurement of a plurality of ionic and gas species at high temperatures. In an illustrative embodiment of my invention for high temperature measurements, the device comprises chemically sensitive layer and electronic acquisition circuitry connected thereto all fixedly attached to the external flat surface of a hermetically sealed ceramic container filled with electrolyte and containing a reference electrode. All but the chemically sensitive surface of said membranes are electrically insulated by the ceramic material. The external surface of the ceramic based device is hermetically sealed against moisture migration.

The use of corrosion resistant platinum metal oxides underlaying the chemically sensitive layers and providing an electrical signal path between the layers and electrical elements on the device is one aspect of the invention that makes the device particularly adaptable to high temperature measurement applications.

As another aspect of the invention, the high temperature properties of the chemically sensitive layer derive from the use of a composite structure employing an outer layer containing polyimide.

BRIEF DESCRIPTION OF THE DRAWINGS

These and other objects, features and advantages of the invention will be more readily apparent from the following detailed description of a preferred embodiment of the invention, which is provided by way of illustration, in which.

DESCRIPTION OF PREFERRED EMBODIMENTS

Figure 1:
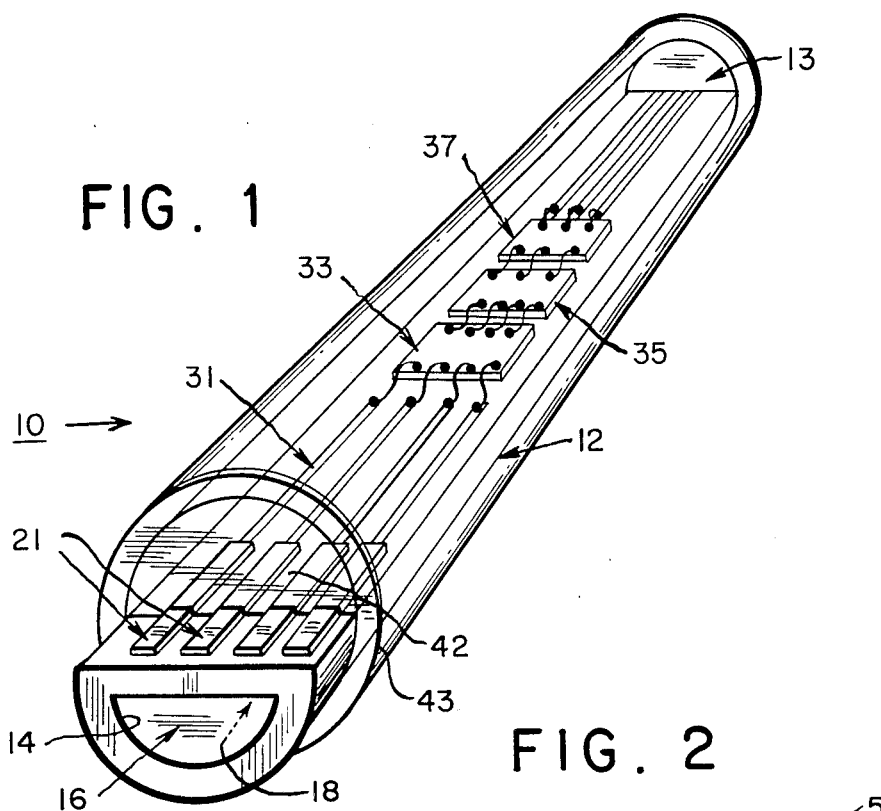
FIG. 1 is a schematic illustration of a high temperature probe of the present invention.

As shown in FIG. 1, a device 10 for the measurement of a plurality of ionic or gas species broadly comprises a ceramic substrate 12, a ceramic plug 16, an electrolyte 18, chemically sensitive membranes 21, electrical signal paths 31, amplifiers 33, a multiplexer 35, and an analog-to-digital converter 37.

Ceramic substrate 12 comprises a ceramic material shaped into a hemispherical cylinder with a closed end 13. Ceramic plug 16 comprises a porous ceramic material shaped into a semi-circle and dimensioned to fit into the open end 14 of ceramic substrate 12. Before ceramic plug 16 is fitted into the open end 14, the ceramic substrate 12 is filled with electrolyte 18.

Electrolyte 18 can be any conventional electrolyte medium for transport of current from chemically sensitive membranes 21 through an ambient solution to a reference electrode located in the electrolyte 18.

Chemically sensitive membranes 21 illustratively are a plurality of chemical or ionic sensitive surfaces each of which develops an electrical potential upon contact with a specific chemical or ion. For pH measurement, for example, the membrane can be sputtered platinum metal oxide. As disclosed in the concurrently filed application, "Ambient Sensing Devices Using Polyimide," measurement of halide or sulfide ion can be accomplished using ion conducting inorganic powders suspended in a polyimide matrix. These powders could be AgCl for chloride analysis, AgBr for bromide analysis, AgI for iodide analysis, $LaF_3$ for fluoride analysis, $Ag_2S$, HgS or $Bi_2S_3$ for sulfide analysis. For gas measurements, the membrane in contact with the ambient can be any heterogeneous gas conducting membrane hardened to high temperature corrosive environments by incorporation of polyimide. Specific examples are polyimide containing polytetrafluoroethylene (PTFE) or zeolite.

High temperature properties of the device are derived from the use of a chemically sensing membrane comprising a mixture of a chemically sensitive compound and the polymer polyimide. Polyimide is known to be stable up to about 500° and has a high degree of hermeticity in hot water. Since heterogeneous membranes employing inorganic compounds in silicone rubber and other polymer matrices are well known to operate adequately at room temperature, the polyimide based membranes make the device 10 advantageously adaptable for use in both room temperature and high temperature mesurement applications. In addition, because polyimide is a material developed as a thin film coating for the electronics industry, these new membranes are advantageously suitable for a thin-film chemically sensitive microelectrode technology.

In accordance with the present invention, signal paths 31 preferably comprise iridium oxide sputtered onto ceramic substrate 12 to a depth approximating 1000 Angstroms although an oxide of any metal from the platinum or rhenium group of metals may advantageously be used. Use of these metal oxides is preferred because they are electrically conducting and are resistant to chemical deterioration at high temperatures. Chemically sensitive membranes 21 are connected to signal paths 31 by forming the membranes on an exposed surface of the signal path as, for example, by thermal evaporation. Platinum and rhenium metal oxides have been found to undergo a reversible oxidation state change by interaction with the appropriate ion or molecule in the chemically sensitive layer.

Amplifiers 33, multiplexer 35, and analog-to-digital converter 37 are integrated circuit devices hardened for high temperature operation. Each amplifier 31 receives the instantaneous signal from one chemically sensitive membrane 21 and generates an amplified, filtered signal at its output proportional to said signal. Multiplexer 35 time multiplexes the analog information from the amplifiers 33. Analog-to-digital converter 37 receives the analog signals from multiplexer 35 and encodes these signals into a digital form for transmission to suitable measurement apparatus (not shown).

Device 10 is completed by ceramic overlay 42 to electrically insulate the electronic package. The outer surface of the overlay is shaped into a semicircle having a radius equal to the radius of the ceramic substrate 12 so that the outer surface of the device 10 is cylindrical in shape. Chemically sensitive membranes 21 are not overlaid to permit exposure of the membranes to the surrounding environment. Hermetic sealant 43 overlays the outside surface of the ceramic cylinder to prevent moisture migration into the device 10.

Figure 2:
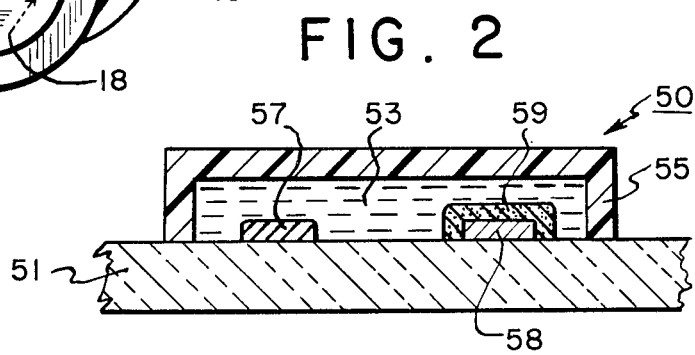
FIGS. 2 and 3 depict illustrative electrodes fabricated in accordance with the invention.

In the present invention, polyimide may also be used to advantage in composite structures to protect different chemical sensing layers from high temperature environments. As shown in FIG. 2, a high temperature gas electrode 50 for use in $CO_2$ gas measurements broadly comprises ceramic substrate 51, aqueous epoxy 53, heterogenous membrane 55, and an electrode pair comprising electrodes 57 and 59.

Aqueous epoxy 53 hardened for high temperature applications comprises NaCl and $NaHCO_3$ and has the chemical property of dissolving $CO_2$ from the ambient causing a change in pH in the layer. Such an aqueous epoxy is formed by making a dispersion of aqueous electrolyte in uncured epoxy, depositing the film, and curing it. The epoxy is separated from the environment by a heterogeneous membrane 55 of the polymer polyimide and polytetrafluoroethylene (PTFE) or zeolite.

Electrode 57 is a chemically sensitive membrane comprising sputtered iridium oxide which develops electrode potential changes when the pH of aqueous layer 53 changes resulting from permeation of $CO_2$ from the ambient. The electrode is sputtered onto ceramic substrate 51 to a depth approximating 1000 Angstroms to fuse the electrode to the substrate.

Iridium oxide is also used as the conductive signal path 58 for electrode 59 which is fused onto ceramic substrate 51 to a depth approximating 1000 Angstroms.

Electrode 59 is AgCl which is used as a reference electrode terminal. The electrode is fused onto sputtered iridium oxide conductive path 58 and ceramic substrate 51.

Figure 3:
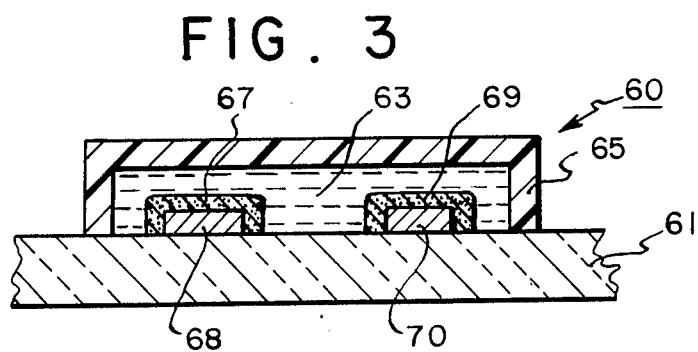
Figure 4:
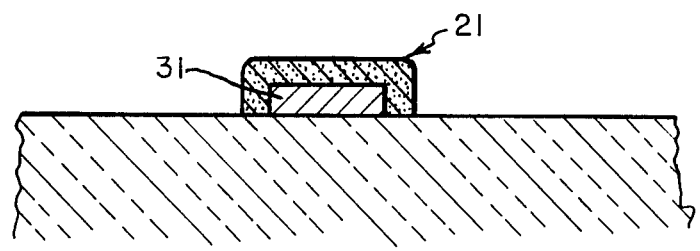

As shown in FIG. 3, a high temperature gas electrode 60 for use in $H_2S$ gas measurements broadly comprises ceramic substrate 61, aqueous epoxy 63, and heterogenous membrane 65, and an electrode pair comprising electrodes 67 and 69.

Aqueous epoxy 63 hardened for high temperature applications comprises NaHS electrolyte and NaCl and has the chemical property of dissolving $H_2S$ causing a change in the sulfide ion concentration. The aqueous epoxy 63 is separated from the environment by a gas permeable heterogeneous membrane 65 of polyimide containing powdered PTFE or zeolite.

Electrode 67 is $Ag_2S$ which has an electrode potential response to a change of sulfide ion concentration in layer 63 resulting from permeation of $H_2S$ gas from the ambient. The electrode is fused onto a sputtered iridium oxide conductive path 68 and substrate 61.

Electrode 69 is a AgCl which is used as a reference electrode terminal. The electrode is fused onto a sputtered iridium oxide conductive path 70 and ceramic substrate 61.

What is claimed is:

1. A device for the measurement of a chemical or an ionic species comprising:
    an amorphous oxide of a metal of the platinum or rhenium groups of metals, and
    a layer of material sensitive to said chemical or ionic species distinct from said amorphous metal oxide formed on said amorphous metal oxide and in electrical contact therewith, said sensitive layer developing an electrical potential upon contact with said chemical or ionic species and said metal oxide transmitting an electrical signal that is a function of said electrical potential.

2. The device of claim 1 wherein said metal oxide is sputtered iridium oxide.

3. The device of claim 1 further comprising a continuous semi-permeable outermost layer that is a mixture of polyimide and either polytetrafluorethylene or zeolite, said outermost layer overlaying said sensitive layer and separating it from an environment in which the device is located but permeable to the chemical or ionic species to be measured.

4. The device of claim 3 wherein said sensitive material is one or more of AgCl, AgBr, AgI, $LaF_3$, $Ag_2S$, HgS and $Bi_2S_3$.

5. A device for the measurement of a chemical or ionic species comprising:
    a chemically sensitive layer that develops an electrical potential representative of the concentration of said species, and
    one or more continuous semi-permeable layers overlaying said sensitive layer and separating it from an environment in which the device is located but permeable to the chemical or ionic species to be measured, wherein the outermost layer contains polyimide.

6. A device for the measurement of activity of a gas species comprising:
    a chemically sensitive layer which develops an electrical potential representative of the concentration of said gas when the device is exposed to said gas;
    means in electrical contact with said chemical sensitive layer for transmitting a signal that is a function of said electrical potential;
    a gas conducting aqueous epoxy medium in electrochemical contact with said chemical sensitive layer, and
    a heterogeneous membrane containing polyimide, said membrane separating said epoxy medium from said gas species and being permeable to said gas species.

7. The device of claim 6 wherein said chemically sensitive layer comprises sputtered iridium oxide and said aqueous epoxy medium comprises epoxy, $H_2O$, $NaHCO_3$, and NaCl.

8. The device of claim 6 wherein said chemically sensitive layer comprises $Ag_2S$ and said aqueous epoxy medium comprises epoxy, $H_2O$, NaHS, and NaCl.

9. The device of claim 6 wherein said means in electrical contact with said chemically sensitive layer comprises a metal oxide as a conductive underlayment, said metal being selected from the platinum and rhenium group of metals; and
    said chemically sensitive layer on and in electrical contact with said underlayment develops an electrical potential upon contact with said gas species and undergoes a reversible reaction with said metal oxide whereby said metal oxide transmits an electrical signal that is a function of the activity of said gas species.

10. The device of claim 6 wherein said heterogeneous membrane comprises polytetrafluoroethylene or zeolite suspended in polyimide.

11. A device for the measurement of a gas species comprising:
    a chemically sensitive layer that develops an electrical potential representative of the concentration of said gas, and
    one or more continuous semi-permeable layers overlaying said sensitive layer and separating it from an environment in which the device is located, wherein the outermost layer is a mixture of polyimide and either polytetrafluoroethylene or zeolite.

12. A device for the measurement of activity of an ionic species comprising:
    a ceramic container filled with an electrolyte medium and containing a reference electrode;
    a chemically sensitive layer mounted on an exterior surface of said container;
    electronic circuitry connected to said layer and mounted on said surface of said container wherein said chemically sensitive layer and said electronic circuitry are made with materials which are stable at high temperatures;
    signal paths interconnecting said chemically sensitive layer and said electronic circuitry;
    a hermetic seal encompassing said electronic circuitry; and
    one or more continuous semi-permeable layers overlaying said sensitive layer and separating it from an environment in which the device is located but permeable to the chemical or ionic species to be measured, wherein the outermost layer contains polyimide.

13. The device of claim 12 wherein said chemically sensitive layer comprises one or more of AgCl, AgBr, AgI, $LaF_3$, $Ag_2S$, HgS and $Bi_2S_3$.

14. The device of claim 12 wherein said electronic circuitry comprises one or more amplifiers.

15. The device of claim 12 comprising a plurality of sensitive layers sensitive to different chemical or ionic species.

16. The device of claim 12 where said signal path comprises a metal from the platinum or rhenium group of metals.

17. The device of claim 12 wherein said signal path comprises iridium oxide.

18. The device of claim 15 wherein said signal path is sputtered onto said ceramic substrate to a depth approximating 1000 Angstroms.

19. A device for the measurement of a chemical or an ionic species comprising:

an amorphous oxide of a metal of the platinum or rhenium groups of metals, a layer of material sensitive to said chemical or ionic species formed on said amorphous metal oxide and in electrical contact therewith, said sensitive layer developing an electrical potential upon contact with said chemical or ionic species and said metal oxide transmitting an electrical signal that is a function of said electrical potential, and one or more continuous semi-permeable layers overlaying said sensitive layer and separating it from an environment in which the device is located but permeable to the chemical or ionic species to be measured, wherein the outermost layer contains polyimide.

20. The device of claim 19 wherein the outermost layer is a mixture of polyimide and either polytetrafluoroethylene or zeolite.

21. The device of claim 19 wherein said sensitive material is one or more of AgCl, AgBr, AgI, $LaF_3$, $Ag_2S$, HgS and $Bi_2S_3$.

22. The device of claim 19 comprising a plurality of sensitive layers sensitive to different chemical or ionic species.

* * * * *